(12) United States Patent
Yamamoto

(10) Patent No.: US 9,435,777 B2
(45) Date of Patent: Sep. 6, 2016

(54) ANALYZING SYSTEM AND CONTROL METHOD THEREOF

(71) Applicant: SHIMADZU CORPORATION, Kyoto-shi, Kyoto (JP)

(72) Inventor: Hideki Yamamoto, Ikeda (JP)

(73) Assignee: SHIMADZU CORPORATION, Kyoto (JP)

( * ) Notice: Subject to any disclaimer, the term of this patent is extended or adjusted under 35 U.S.C. 154(b) by 313 days.

(21) Appl. No.: 14/083,909

(22) Filed: Nov. 19, 2013

(65) Prior Publication Data
US 2014/0157875 A1    Jun. 12, 2014

(30) Foreign Application Priority Data

Dec. 11, 2012    (JP) .................................. 2012-270029

(51) Int. Cl.
G01N 30/86    (2006.01)
G01N 33/00    (2006.01)

(52) U.S. Cl.
CPC ........... *G01N 30/86* (2013.01); *G01N 30/8658* (2013.01); *G01N 33/00* (2013.01)

(58) Field of Classification Search
CPC .............................. G01N 33/00; G01N 30/86
See application file for complete search history.

(56) References Cited

U.S. PATENT DOCUMENTS

2007/0239829 A1*  10/2007  Verseput ................. G06F 17/50
                                                 709/204
2012/0096919 A1*   4/2012  Choikhet ............... G01N 30/24
                                                 73/1.02

FOREIGN PATENT DOCUMENTS

| JP | 2006071287 A | 3/2006 |
| JP | 2008268048 A | 11/2008 |
| JP | 2009047592 A | 3/2009 |
| JP | 2011-185794 A | 9/2011 |

OTHER PUBLICATIONS

English Machine Translation of Takeshi, JP 2011-109402 A, Feb. 6, 2011, Translated Jun. 2016.*

* cited by examiner

*Primary Examiner* — Hezron E Williams
*Assistant Examiner* — David Z Huang
(74) *Attorney, Agent, or Firm* — Sughrue Mion, PLLC

(57) ABSTRACT

There are provided an analyzing system and a control method thereof which are capable of preventing a discrepancy from arising between a condition set by using a condition setting device and a condition set by using an operation section of each unit. Setting of a condition using the operation section is restricted at each unit controlled by a control device at least when transmission/reception of data is being performed between the condition setting device and the control device. Accordingly, a different condition is not set by using the operation section of each unit when data of a condition set by using the condition setting device is transmitted to the control device. Thus, a discrepancy may be prevented from arising between the condition set by using the condition setting device and a condition set by using the operation section of each unit.

8 Claims, 4 Drawing Sheets

ANALYZING SYSTEM AND CONTROL METHOD THEREOF

BACKGROUND OF THE INVENTION

1. Field of the Invention

The present invention relates to an analyzing system and a control method thereof. The analyzing system includes a plurality of units, a condition setting device and a control device. The plurality of units are for operating to analyze a sample. The condition setting device is for setting a condition regarding operations of the plurality of units. The control device is capable of performing transmission/reception of data with the plurality of units and the condition setting device. The control device is for controlling the plurality of units according to the condition set by the condition setting device.

2. Description of the Related Art

For example, according to a certain analyzing device such as a liquid chromatograph, sections of the analyzing device are unitized on a per-function basis, and the operation of each unit is controlled by a control device. With this type of analyzing device, it is possible to connect a condition setting device configured from a computer, for example, to the control device, and to thereby configure an analyzing system where the control device controls each unit according to a condition set by using the condition setting device (for example, see JP-A-2011-185794).

According to such an analyzing system, a plurality of units that operate to analyze a sample, such as a liquid delivery unit, an autosampler, a column oven, a detector and the like, are controlled by one control device according to a condition set by using the condition setting device. Software for setting a condition regarding the operation of each unit, for example, is installed on the condition setting device, and data of a condition set by using the software is transmitted to the control device.

With the analyzing system capable of setting a condition regarding the operation of each unit using the condition setting device as described above, the condition setting device may be installed at a location away from the location where the analyzing device is installed (for example, a laboratory), and a condition regarding the operation of each unit may be set by remote operation.

Some of the analyzing systems as described above have an operation section provided to each unit, and a condition regarding the operation of each unit may be set by operating the operation section. In this case, a discrepancy may arise between the condition set by using the condition setting device and the condition set by using the operation section of each unit, and analysis may be performed under a condition not intended by a user. This may result in various negative effects, such as not being able to obtain an accurate analysis result, an error occurring on software, and the like.

Also, in a case of a configuration allowing transmission/reception of data between a plurality of condition setting devices and a control device, normally, when one of the condition setting devices is transmitting data to the control device, transmission of data from other condition setting devices to the control device is restricted. In this case, there are problems that the control device cannot identify with which condition setting device transmission/reception of data is being performed, and also, that other condition setting devices cannot identify which condition setting device is transmitting data to the control device.

Thus, the relationship of the devices performing transmission/reception of data cannot be clearly grasped without performing, at the condition setting device transmitting data to the control device, an operation of checking the contents displayed on a display section, for example, and this checking operation is burdensome. Particularly, in a case where the condition setting device is installed at a location away from the location where the analyzing device is installed (for example, a laboratory), there is a problem that a user performing the analysis operation at the analyzing device cannot easily perform the checking operation as described above.

SUMMARY OF THE INVENTION

The present invention has been made in view of the above circumstances, and an object thereof is to provide an analyzing system and a control method thereof that are capable of preventing a discrepancy from arising between a condition set by using a condition setting device and a condition set by using an operation section of each unit. Also, a further object of the present invention is to provide an analyzing system and a control method thereof that allow clearer grasping of the relationship of devices performing transmission/reception of data with each other.

An analyzing system according to the present invention includes a plurality of units, a condition setting device and a control device. The plurality of units are for operating to analyze a sample. The condition setting device is for setting a condition regarding operations of the plurality of units. The control device is capable of performing transmission/reception of data with the plurality of units and the condition setting device. The control device is for controlling the plurality of units according to the condition set by the condition setting device. The plurality of units include operation sections allowing setting of conditions regarding operations of respective units. Setting of a condition using the operation section is restricted at least when transmission/reception of data is being performed between the condition setting device and the control device.

According to such a configuration, setting of a condition using the operation section at each unit controlled by the control device is restricted at least when transmission/reception of data is being performed between the condition setting device and the control device. Accordingly, a different condition is not set by using the operation section of each unit when data of a condition set by using the condition setting device is transmitted to the control device. Thus, a discrepancy may be prevented from arising between the condition set by using the condition setting device and a condition set by using the operation section of each unit.

The control device may include a display section capable of displaying identification information of the condition setting device performing transmission/reception of data with the control device.

According to such a configuration, the condition setting device performing transmission/reception of data with the control device may be grasped by checking the identification information displayed on the display section of the control device. Accordingly, the relationship of devices performing transmission/reception of data with each other may be more clearly grasped. Also, the condition setting device performing transmission/reception of data with the control device may be easily grasped at the control device.

The analyzing system may include a plurality of the condition setting devices each including a display section. In a case where an instruction to perform transmission/reception of data with the control device is issued at a second condition setting device when a first condition setting device is performing transmission/reception of data with the control device, a notice to an effect that transmission/reception of data with the control device cannot be performed may be displayed on the display section of the second condition setting device.

According to such a configuration, in a case where an instruction to perform transmission/reception of data with the control device is issued at the second condition setting device while transmission/reception of data is being performed between the first condition setting device and the control device, a notice to the effect that transmission/reception of data with the control device cannot be performed may be clearly grasped based on the display on the display section of the second condition setting device.

The notice to an effect that transmission/reception of data with the control device cannot be performed and identification information of the first condition setting device performing transmission/reception of data with the control device may be displayed on the display section of the second condition setting device.

According to such a configuration, the condition setting device (the first condition setting device) performing transmission/reception of data with the control device may be grasped at the second condition setting device which is not allowed to perform transmission/reception of data with the control device, by checking the identification information displayed on the display section. Accordingly, the relationship of devices performing transmission/reception of data with each other may be more clearly grasped.

A notice to an effect that an instruction to perform transmission/reception of data with the control device has been issued at the second condition setting device may be displayed on the display section of the first condition setting device.

According to such a configuration, in a case where an instruction to perform transmission/reception of data with the control device is issued at the second condition setting device while transmission/reception of data is being performed between the first condition setting device and the control device, this may be clearly grasped based on the display on the display section of the first condition setting device.

A control method of an analyzing system according to the present invention is for the analyzing system including a plurality of units, a condition setting device and a control device. The plurality of units are for operating to analyze a sample. The condition setting device is for setting a condition regarding operations of the plurality of units. The control device is capable of performing transmission/reception of data with the plurality of units and the condition setting device. The control device is for controlling the plurality of units according to the condition set by the condition setting device. The method includes performing a process for restricting setting of conditions regarding operations of respective units using operation sections included in the plurality of units at least when transmission/reception of data is being performed between the condition setting device and the control device.

According to the present invention, since a different condition is not set by using the operation section of each unit when data of a condition set by using the condition setting device is transmitted to the control device, a discrepancy may be prevented from arising between the condition set by using the condition setting device and a condition set by using the operation section of each unit. Also, in a case where identification information of a device performing transmission/reception of data is displayed on a display section of the control device or a display section of the condition setting device, the relationship of devices performing transmission/reception of data with each other may be more clearly grasped.

DETAILED DESCRIPTION OF THE PREFERRED EMBODIMENTS

Figure 1:
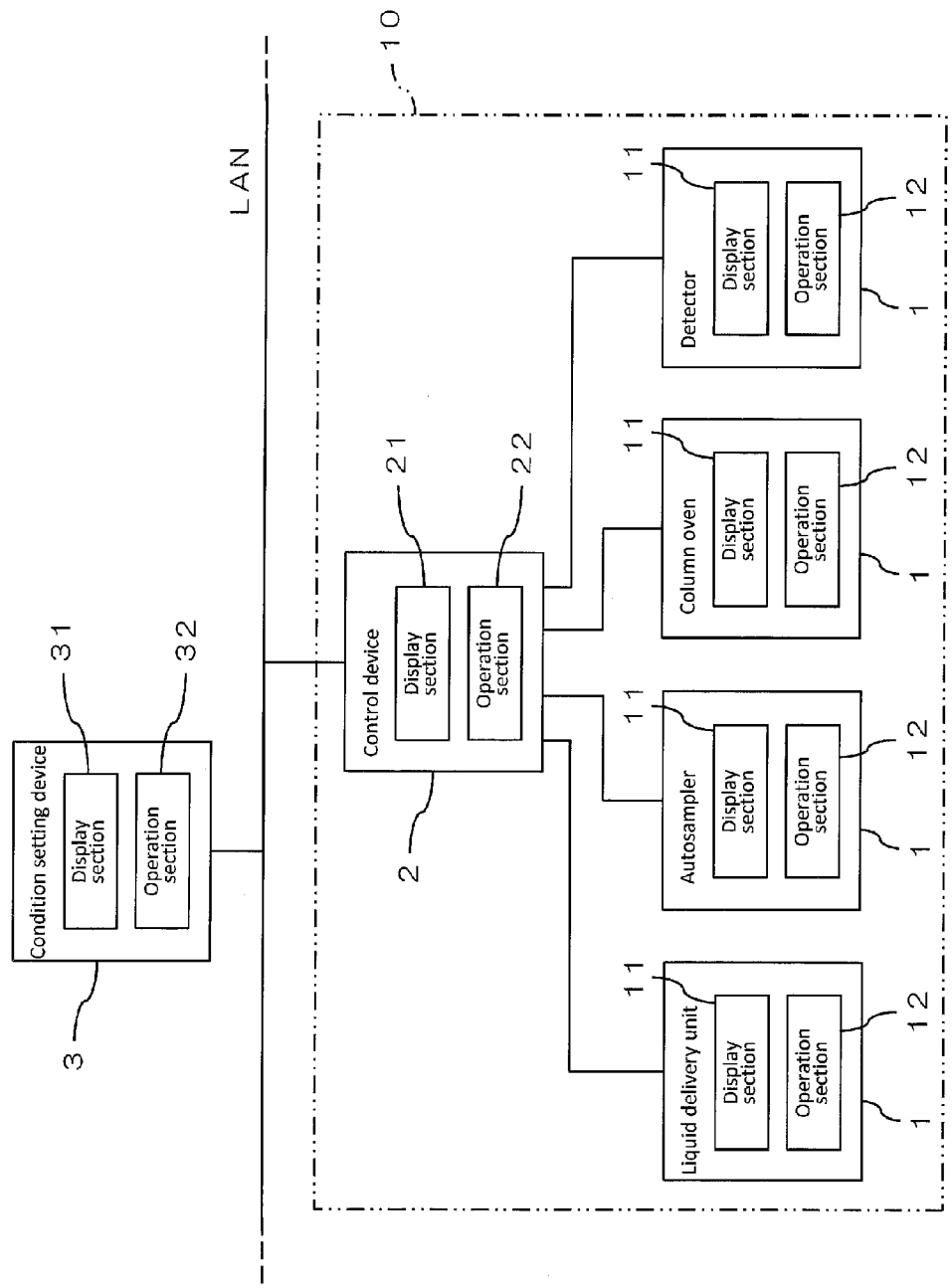
FIG. 1 is a block diagram showing a configuration example of an analyzing system according to an embodiment of the present invention.

FIG. 1 is a block diagram showing a configuration example of an analyzing system according to an embodiment of the present invention. This analyzing system includes a plurality of units 1, a control device 2, a condition setting device 3 and the like, and the plurality of units 1 and the control device 2 configure an analyzing device 10 such as a liquid chromatograph, for example. Additionally, the analyzing device 10 is not limited to a liquid chromatograph.

The plurality of units 1 are sections of the analyzing device 10 unitized on a per-function basis, and each operates to analyze a sample. Each unit 1 includes a display section 11, an operation section 12, or the like. The display section 11 may be configured from an LCD (Liquid Crystal Display), for example. Also, the operation section 12 may be configured from operation keys, a touch panel or the like, for example.

In this example, the plurality of units 1 are each configured from a liquid delivery unit, an autosampler, a column oven, a detector or the like, for example. The function of each unit 1 is a well-known art, and detailed description thereof will not be given. It should be noted that the plurality of units 1 are not limited to the above configurations, and may be configured from units 1 and the like for realizing other functions.

The control device 2 is configured to include a CPU (Central Processing Unit), for example, and the plurality of units 1 connected to the control device 2 may be controlled by the CPU executing a program. This control device 2 configures a system controller for collectively controlling the plurality of units 1, and the units 1 may be made to operate at an appropriate timing in conjunction with each other by the control using the control device 2, and analysis may be performed in a desirable manner.

For example, the control device 2 may transmit/receive data to/from each of the units 1 while switching channels at predetermined intervals, and thus, may control the operation of each unit 1 with a smaller communication load. The control device 2 includes a display section 21, an operation section 22, or the like. The display section 21 may be configured from a liquid crystal display, for example. Also, the operation section 22 may be configured from operation keys, a touch panel or the like, for example.

The condition setting device 3 is configured from a personal computer, for example, and includes a display section 31, an operation section 32, or the like. The display section 31 may be configured from a liquid crystal display, for example. Also, the operation section 32 may be configured from a keyboard, a mouse or the like, for example. With this condition setting device 3, conditions regarding operations of the plurality of units 1 may be set by operating the operation section 32.

For example, software for setting conditions regarding the operations of the plurality of units 1 is installed on the condition setting device 3, and a condition may be set by operating the operation section 32 while checking a screen which is displayed on the display section 31 when the software is activated. The condition setting device 3 is not directly connected to the plurality of units 1, but is indirectly connected thereto via the control device 2. In this example, the control device 2 and the condition setting device 3 are capable of communication via a network line such as a LAN (Local Area Network).

As described above, the control device 2 is capable of transmitting/receiving data with the plurality of units 1 and the condition setting device 3. Accordingly, the control device 2 is capable of controlling the plurality of units 1 according to conditions set by the condition setting device 3. On the other hand, a condition regarding the operation of each unit 1 may also be set by operating the operation section 12 provided to each unit 1.

In the present embodiment, setting of a condition using the operation section 12 of each unit 1 connected to the control device 2 is restricted at least when data is being transmitted/received between the condition setting device 3 and the control device 2.

Figure 2:
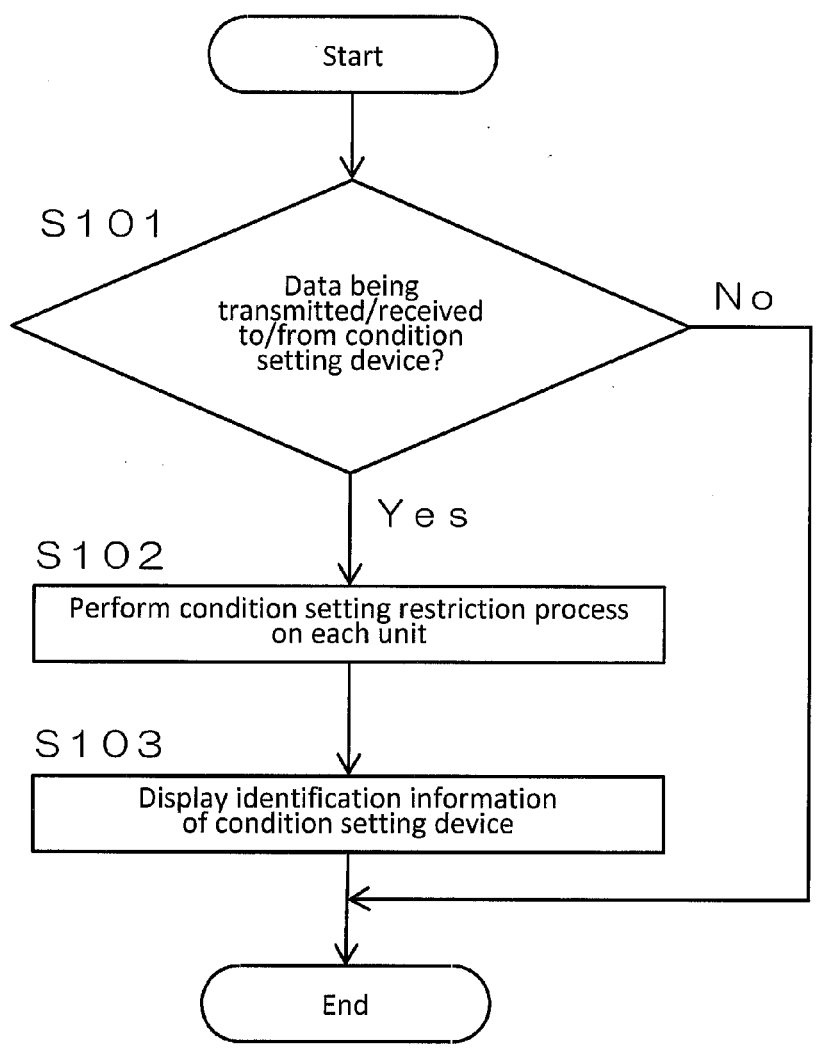
FIG. 2 is a flow chart showing an example of a process of a control device in FIG. 1.

FIG. 2 is a flow chart showing an example of a process of the control device 2 in FIG. 1. When data is being transmitted/received between the control device 2 and the condition setting device 3 (step S101; YES), the control device 2 performs a process of restricting setting of a condition using the operation section 12 of each unit 1 connected to the control device 2 (step S102).

In this example, when a user tries to operate the operation section 12 of a unit 1 connected to the control device 2 which is performing transmission/reception of data with the condition setting device 3, a notice that the condition setting device 3 is currently connected, such as "connected by PC", is displayed on the display section 11 of the unit 1, so that the user cannot operate the operation section 12.

Also, identification information of the condition setting device 3 performing transmission/reception of data with the control device 2 is displayed on the display section 21 of the control device 2 currently performing transmission/reception of data with the condition setting device 3 (step S103). The identification information is, for example, an identifier of the condition setting device 3, and this identification information may be received from the condition setting device 3. It should be noted that the identification information is not limited to the identifier of the condition setting device 3.

As described above, according to the present embodiment, setting of a condition using the operation section 12 at each unit 1 controlled by the control device 2 is restricted at least when data is being transmitted/received between the condition setting device 3 and the control device 2. Accordingly, a different condition is not set by using the operation section 12 of each unit 1 while data of a condition set by using the condition setting device 3 is transmitted to the control device 2. Thus, a discrepancy may be prevented from arising between a condition set by using the condition setting device 3 and a condition set by using the operation section 12 of each unit 1.

Also, according to the present embodiment, the condition setting device 3 performing transmission/reception of data with the control device 2 may be grasped by checking the identification information displayed on the display section 21 of the control device 2. The relationship of devices performing transmission/reception of data with each other may thereby be more clearly grasped. Also, the condition setting device 3 performing transmission/reception of data with the control device 2 may be easily grasped at the control device 2.

Figure 3:
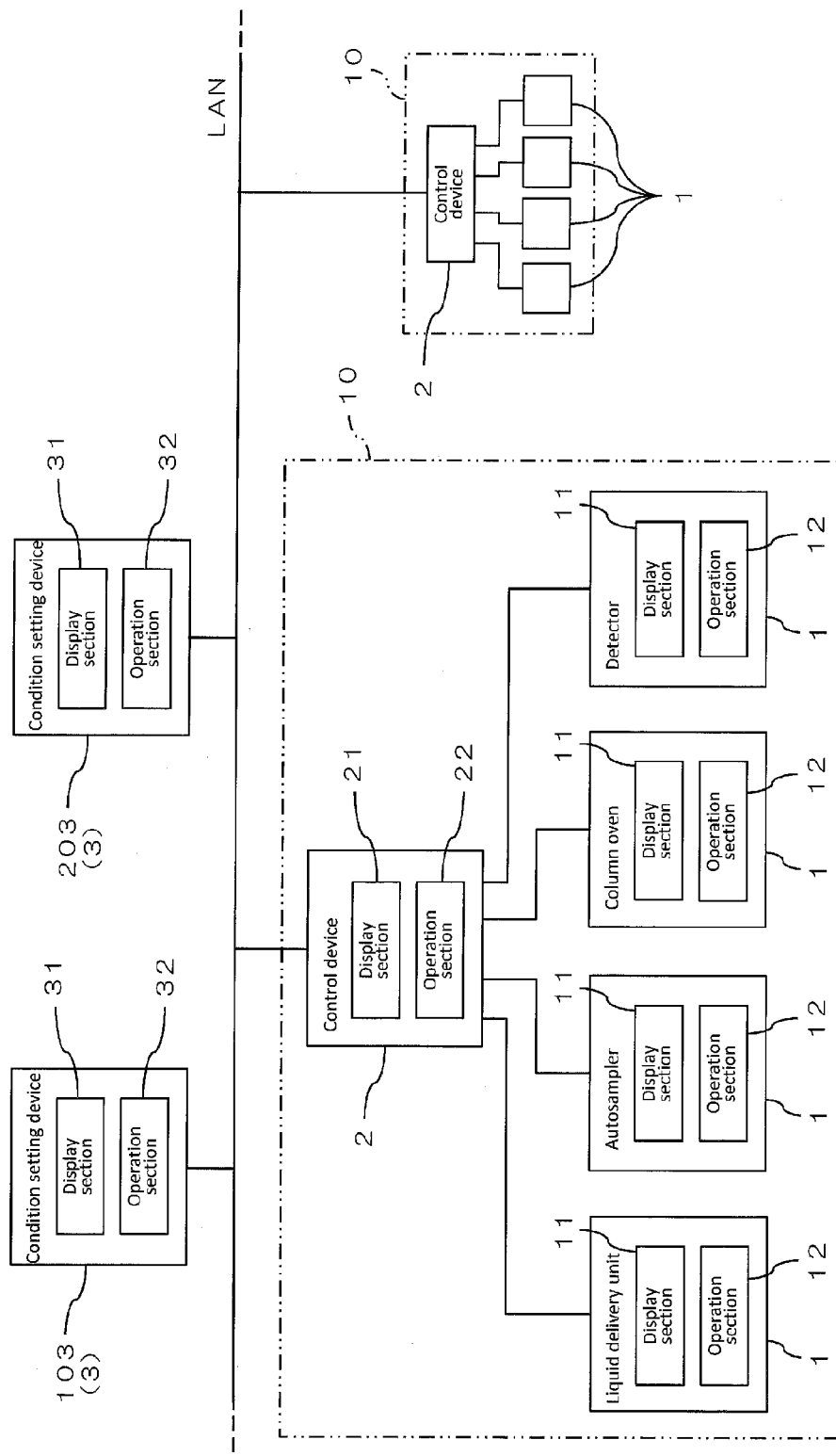
FIG. 3 is a block diagram showing a configuration example of an analyzing system according to another embodiment.

FIG. 3 is block diagram showing a configuration example of an analyzing system according to another embodiment. With this analyzing system, a plurality of control devices 2 and a plurality of condition setting devices 3 may be connected one-to-one in arbitrary combination via a network line such as a LAN, and communication may be performed between the devices. Each control device 2 has connected thereto a plurality of units 1 to be controlled by the control device 2, and the control devices 2 configure separate analyzing devices 10.

The concrete configurations of each unit 1, each control device 2 and each condition setting device 3 are the same as those described in the above embodiment, and detailed description thereof will not be given. In the following, the present embodiment will be concretely described taking an arbitrary condition setting device 3 as a first condition setting device 103 and an arbitrary condition setting device 3 different from the first condition setting device 103 as a second condition setting device 203.

Figure 4:
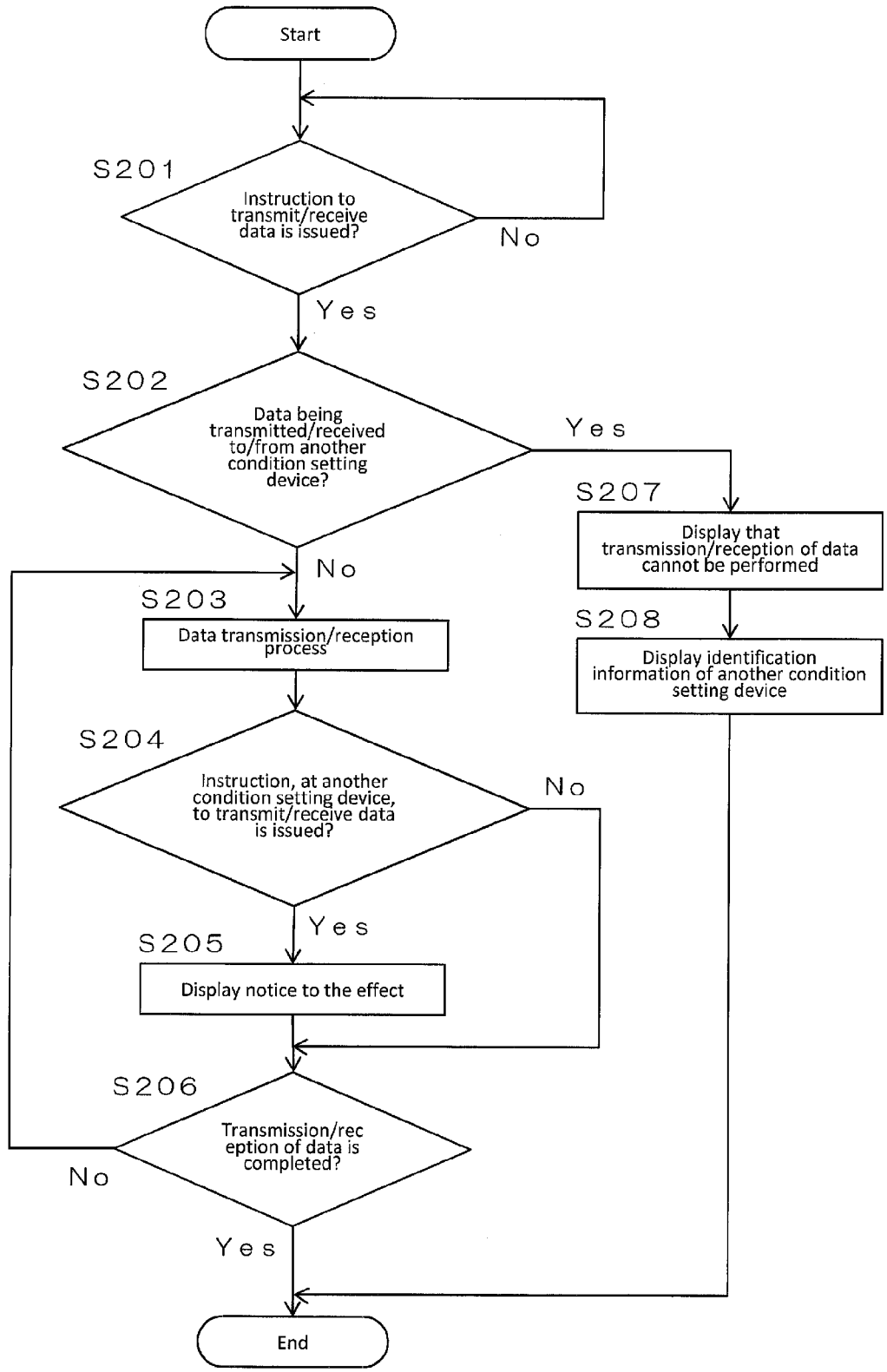
FIG. 4 is a flow chart showing an example of a process of a condition setting device in FIG. 3.

FIG. 4 is a flow chart showing an example of a process of the condition setting device 3 in FIG. 3. In the present embodiment, the process of each control device 2 is performed in the manner as illustrated in FIG. 2 described above. On the other hand, the process of each condition setting device 3 is performed in the manner as illustrated in FIG. 4.

In the case where an instruction to perform transmission/reception of data with the control device 2 is issued using, for example, software installed on the condition setting device 3 (step S201; Yes), the condition setting device 3 determines whether the control device 2 is performing transmission/reception of data with another condition setting device 3 or not (step S202). This determination may be performed based on a response signal from the control device 2, for example.

In the case where the control device 2 which is to transmit/receive data is not performing transmission/reception of data with another condition setting device 3 (step S202; No), the condition setting device 3 performs a process for transmitting/receiving data with the control device 2 (step S203). During such data reception processing, whether an instruction to perform transmission/reception of data with the control device 2 has been issued at another condition setting device 3 or not is monitored (step S204) until transmission/reception of data is completed (until Yes is obtained in step S206).

This determination of whether an instruction as mentioned above has been issued at another condition setting device 3 or not may be performed based on a response signal from the control device 2, for example. Then, in the case where such an instruction has been issued (step S204; Yes), a notice to the effect is displayed on the display section 31 of the condition setting device 3 which is currently performing the process of receiving data. That is, in a case where an instruction to perform transmission/reception of data with an arbitrary control device 2 is issued at the second condition setting device 203 while the first condition setting device 103 is performing transmission/reception of data with the control device 2, a notice to the effect is displayed on the display section 31 of the first condition setting device 103.

Such display may be display of "Connection attempted by another PC", for example, or a configuration is also possible where an identifier or the like is included as the identification information of another condition setting device 3 (the second condition setting device 203). This identification information may be received from the control device 2. It should be noted that the identification information is not limited to the identifier of the condition setting device 3.

Accordingly, in a case where an instruction to perform transmission/reception of data with the control device 2 is issued at the second condition setting device 203 while transmission/reception of data is being performed between the first condition setting device 103 and the control device 2, this may be clearly grasped based on the display on the display section 31 of the first condition setting device 103.

On the other hand, in the case where a control device 2 with which data is to be transmitted/received is performing transmission/reception of data with another condition setting device 3 (step S202; Yes), the condition setting device 3 displays on the display section 31 a notice to the effect that transmission/reception of data with the control device 2 cannot be performed (step S207).

That is, in the case where an instruction to perform transmission/reception of data with the control device 2 is issued at the second condition setting device 203 while transmission/reception of data is being performed between the first condition setting device 103 and the control device 2, a notice to the effect that transmission/reception of data with the control device 2 cannot be performed is displayed on the display section 31 of the second condition setting device 203.

Accordingly, in the case where an instruction to perform transmission/reception of data with the control device 2 is issued at the second condition setting device 203 while transmission/reception of data is being performed between the first condition setting device 103 and the control device 2, a notice to the effect that transmission/reception of data with the control device 2 cannot be performed may be clearly grasped based on the display on the display section 31 of the second condition setting device 203.

Also, the condition setting device 3 displays, on the display section 31, the identification information of another condition setting device 3 which is already performing transmission/reception of data with the control device 2 with which the afore-mentioned condition setting device 3 is attempting to perform transmission/reception of data (step S208).

That is, in the case where an instruction to perform transmission/reception of data with the control device 2 is issued at the second condition setting device 203 while transmission/reception of data is being performed between the first condition setting device 103 and the control device 2, a notice to the effect that transmission/reception of data with the control device 2 cannot be performed, and the identification information of the first condition setting device 103 which is performing transmission/reception of data with the control device 2 are displayed on the display section 31 of the second condition setting device 203.

Accordingly, by checking the identification information displayed on the display section 31 at the second condition setting device 203 which is not allowed to perform transmission/reception of data with the control device 2, the condition setting device (the first condition setting device 103) which is performing transmission/reception of data with the control device 2 may be grasped. Thus, the relationship of devices performing transmission/reception of data with each other may be more clearly grasped.

Moreover, it is also possible to omit display of the identification information of another condition setting device 3 as described above. That is, the display on the display section 31 of the second condition setting device 203 may be display such as "Another PC is connecting. This PC is not allowed connection", or a configuration is also possible according to which an identifier or the like is included as the identification information of another condition setting device 3 (the first condition setting device 103). This identification information may be received from the control device 2. It should be noted that the identification information is not limited to the identifier of the condition setting device 3.

According to the above embodiment, the operation section 12 of each unit 1 connected to the control device 2 cannot be operated while transmission/reception of data is being performed between the condition setting device 3 and the control device 2, but this configuration is not restrictive, and any configuration is possible as long as setting of a condition using the operation section 12 of each unit 1 is restricted. For example, instead of a configuration completely prohibiting the operation of the operation section 12 of each unit 1, a configuration prohibiting only setting of a condition or a configuration restricting setting of some conditions may be adopted.

Also, setting of a condition using the operation section 12 of each unit 1 is restricted at least when transmission/reception of data is being performed between the condition setting device 3 and the control device 2, and a configuration may also be possible according to which setting of a condition using the operation section 12 of each unit 1 is restricted while software for setting a condition is activated on the condition setting device 3, for example.

In this case, a configuration may be possible according to which restriction on setting of a condition using the operation section 12 of each unit 1 is released when an operation of ending the software is performed at the condition setting device 3. Furthermore, a configuration may also be possible according to which, even when an operation for ending the software is performed at the condition setting device 3, if data is being transmitted from one of the units 1 to the control device 2, setting of a condition using the operation section 12 of each unit 1 is maintained restricted.

In the above embodiment, a configuration where a plurality of units 1 and the control device 2 for controlling these units 1 are configured separately, and where the display sections 11 and 21 are provided thereto has been described. However, such a configuration is not restrictive, and a plurality of units 1 and the control device 2 may integrally configure the analyzing device 10, and display the same as the display on the display section 11 of each unit 1 or the display section 21 of the control device 2 may be performed on one display section provided to the analyzing device 10.

Furthermore, a program to be executed by one of the devices configuring the analyzing system of the present invention, such as a program used for processing by the control device 2 as illustrated in FIG. 2 or a program used for processing by the condition setting device 3 as illustrated in FIG. 4, may be provided as a control program. In this case, this program may be provided being stored in a storage medium, or the program itself may be provided.

What is claimed is:

1. An analyzing system comprising:
    a plurality of units for operating to analyze a sample;

a condition setting device for setting a condition regarding operations of the plurality of units; and a control device capable of performing transmission/reception of data with the plurality of units and the condition setting device, the control device being for controlling the plurality of units according to the condition set by the condition setting device, wherein the plurality of units include operation sections allowing setting of conditions regarding operations of respective units, and setting of a condition using the operation section is restricted at least when transmission/reception of data is being performed between the condition setting device and the control device.

2. The analyzing system according to claim 1, wherein the control device includes a display section capable of displaying identification information of the condition setting device performing transmission/reception of data with the control device.

3. The analyzing system according to claim 1, comprising:

a plurality of the condition setting devices each including a display section, wherein, in a case where an instruction to perform transmission/reception of data with the control device is issued at a second condition setting device when a first condition setting device is performing transmission/reception of data with the control device, a notice to an effect that transmission/reception of data with the control device cannot be performed is displayed on the display section of the second condition setting device.

4. The analyzing system according to claim 3, wherein the notice to an effect that transmission/reception of data with the control device cannot be performed and identification information of the first condition setting device performing transmission/reception of data with the control device are displayed on the display section of the second condition setting device.

5. The analyzing system according to claim 3, wherein a notice to an effect that an instruction to perform transmission/reception of data with the control device has been issued at the second condition setting device is displayed on the display section of the first condition setting device.

6. The analyzing system according to claim 1, wherein the setting of a condition using the operation section is restricted at least when data of a condition set by using the condition setting device is transmitted to the control device between the condition setting device and the control device.

7. A control method of an analyzing system including a plurality of units for operating to analyze a sample, a condition setting device for setting a condition regarding operations of the plurality of units, and a control device capable of performing transmission/reception of data with the plurality of units and the condition setting device, the control device being for controlling the plurality of units according to the condition set by the condition setting device, the method comprising:

performing a process for restricting setting of conditions regarding operations of respective units using operation sections included in the plurality of units at least when transmission/reception of data is being performed between the condition setting device and the control device.

8. The control method of an analyzing system according to claim 7, wherein the process for restricting setting of conditions regarding operations of respective units using operation sections included in the plurality of units is performed at least when data of a condition set by using the condition setting device is transmitted to the control device between the condition setting device and the control device.

* * * * *